(12) United States Patent
Scaringe et al.

(10) Patent No.: US 9,881,478 B1
(45) Date of Patent: Jan. 30, 2018

(54) WEB-BASED, PLUG AND PLAY WIRELESS REMOTE MONITORING DIAGNOSTIC AND SYSTEM HEALTH PREDICTION SYSTEM

(71) Applicants: Robert P. Scaringe, Rockledge, FL (US); Robert Paul Roth, Rockledge, FL (US); Daniel Lambert, Merritt Island, FL (US); Erik P. Thomas, Cumberland, ME (US); Chad L. Carff, Rockledge, FL (US)

(72) Inventors: Robert P. Scaringe, Rockledge, FL (US); Robert Paul Roth, Rockledge, FL (US); Daniel Lambert, Merritt Island, FL (US); Erik P. Thomas, Cumberland, ME (US); Chad L. Carff, Rockledge, FL (US)

(73) Assignee: MAINSTREAM ENGINEERING CORPORATION, Rockledge, FL (US)

( * ) Notice: Subject to any disclaimer, the term of this patent is extended or adjusted under 35 U.S.C. 154(b) by 0 days.

(21) Appl. No.: 14/795,401

(22) Filed: Jul. 9, 2015

Related U.S. Application Data

(62) Division of application No. 13/226,520, filed on Sep. 7, 2011, now Pat. No. 9,168,315.

(51) Int. Cl.
*F25B 49/02* (2006.01)
*G08B 21/18* (2006.01)

(52) U.S. Cl.
CPC ...... *G08B 21/187* (2013.01); *F25B 2345/003* (2013.01); *F25B 2500/08* (2013.01); *F25B 2500/222* (2013.01); *F25B 2700/21152* (2013.01); *F25B 2700/21163* (2013.01)

(58) Field of Classification Search
CPC ............ F25B 2345/003; F25B 2500/08; F25B 2500/222; F25B 2700/21152; F25B 2700/21163
See application file for complete search history.

(56) References Cited

U.S. PATENT DOCUMENTS

| | | | |
|---|---|---|---|
| 3,233,822 A | | 2/1966 | Comstock et al. |
| 4,727,320 A | * | 2/1988 | Brennan ................ G01R 31/34 |
| | | | 324/545 |
| 5,381,669 A | | 1/1995 | Bahel et al. |
| 5,689,963 A | | 11/1997 | Bahel et al. |
| 6,385,510 B1 | | 5/2002 | Hoog et al. |

(Continued)

OTHER PUBLICATIONS

G.Van Wylen and R.Sonntag, Foundamentals of Classical Thermodynamics, p. 37 (John Wiley & Sons, 2nd ed., SI version 1978)).

*Primary Examiner* — Jonathan Bradford

(57) ABSTRACT

A diagnostic monitoring system and method is employed for one or more vapor compression systems such as air conditioners and heat pumps having a compressor, an indoor air handler fan coil and an outdoor condensor. Temperature, voltage and current sensors are provided at the outdoor condensor to determine that at least one vapor compression system is operating properly. Data obtained from the sensors is wirelessly transmitted to a receiving-device for use by the systems' custodian or repair service provider and includes information concerning an occurrence of periods when one or more of the vapor compression systems are operating at an abnormal state.

9 Claims, 11 Drawing Sheets

Basic high-level diagram for one embodiment of the OCU-ED

(56) References Cited

U.S. PATENT DOCUMENTS

| | | | |
|---|---|---|---|
| 7,114,343 B2 * | 10/2006 | Kates | F24F 3/1603 |
| | | | 165/11.1 |
| 7,469,546 B2 | 12/2008 | Kates | |
| 7,596,959 B2 | 10/2009 | Singh et al. | |
| 7,792,256 B1 | 9/2010 | Arledge et al. | |
| 8,132,419 B2 | 3/2012 | Yonemori et al. | |
| 8,590,325 B2 | 11/2013 | Pham | |
| 2006/0042276 A1 * | 3/2006 | Doll | F25B 49/005 |
| | | | 62/129 |
| 2006/0137368 A1 * | 6/2006 | Kang | F25B 45/00 |
| | | | 62/149 |
| 2008/0077260 A1 | 3/2008 | Porter et al. | |
| 2010/0101250 A1 * | 4/2010 | Jayanth | B25J 9/1687 |
| | | | 62/126 |

* cited by examiner

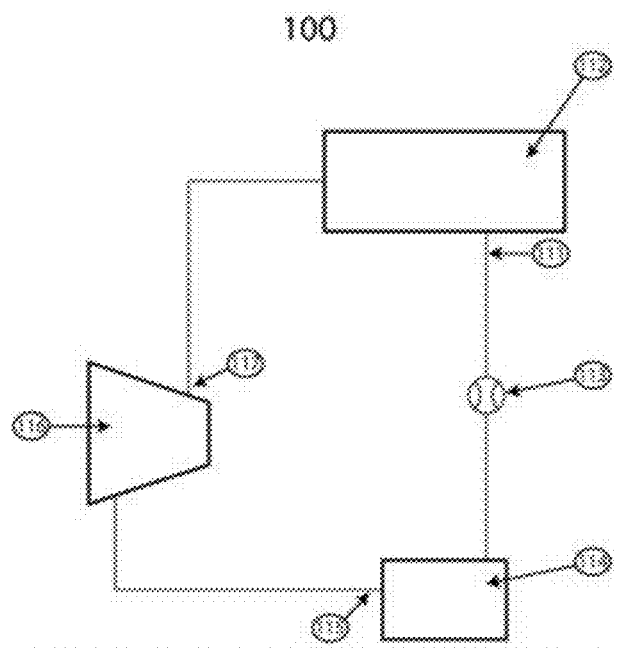
Figure 1: Basic vapor-compression cycle diagram

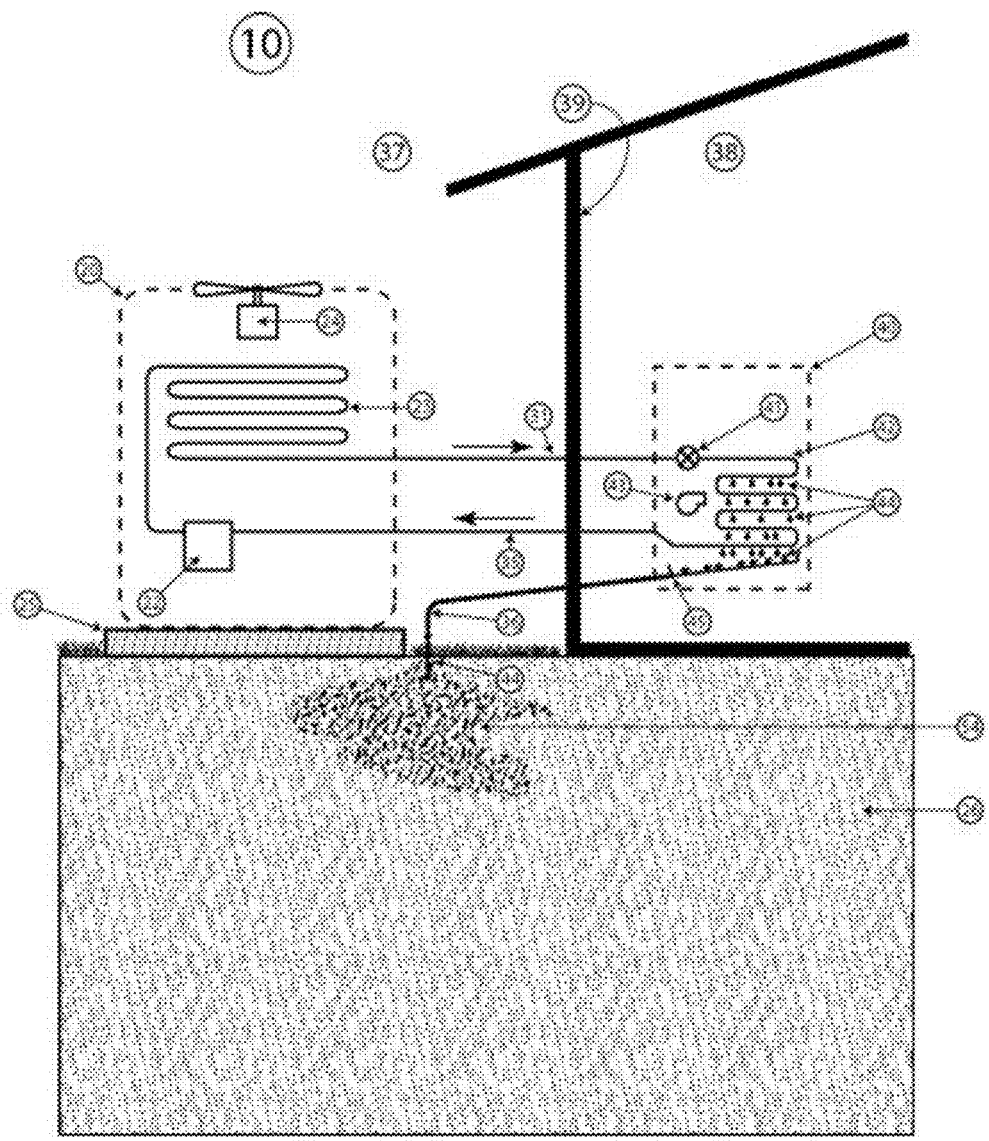
Figure 2: Split system operating in cooling mode

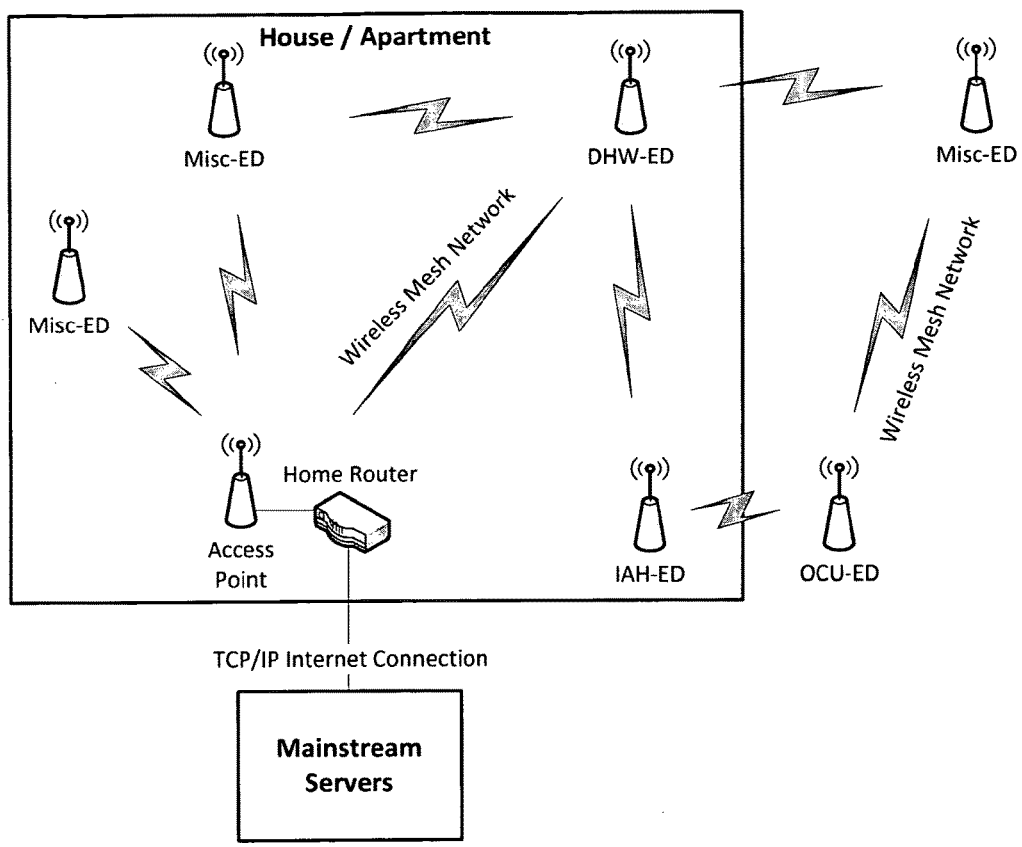
Figure 3: Information flow in the currently preferred embodiment

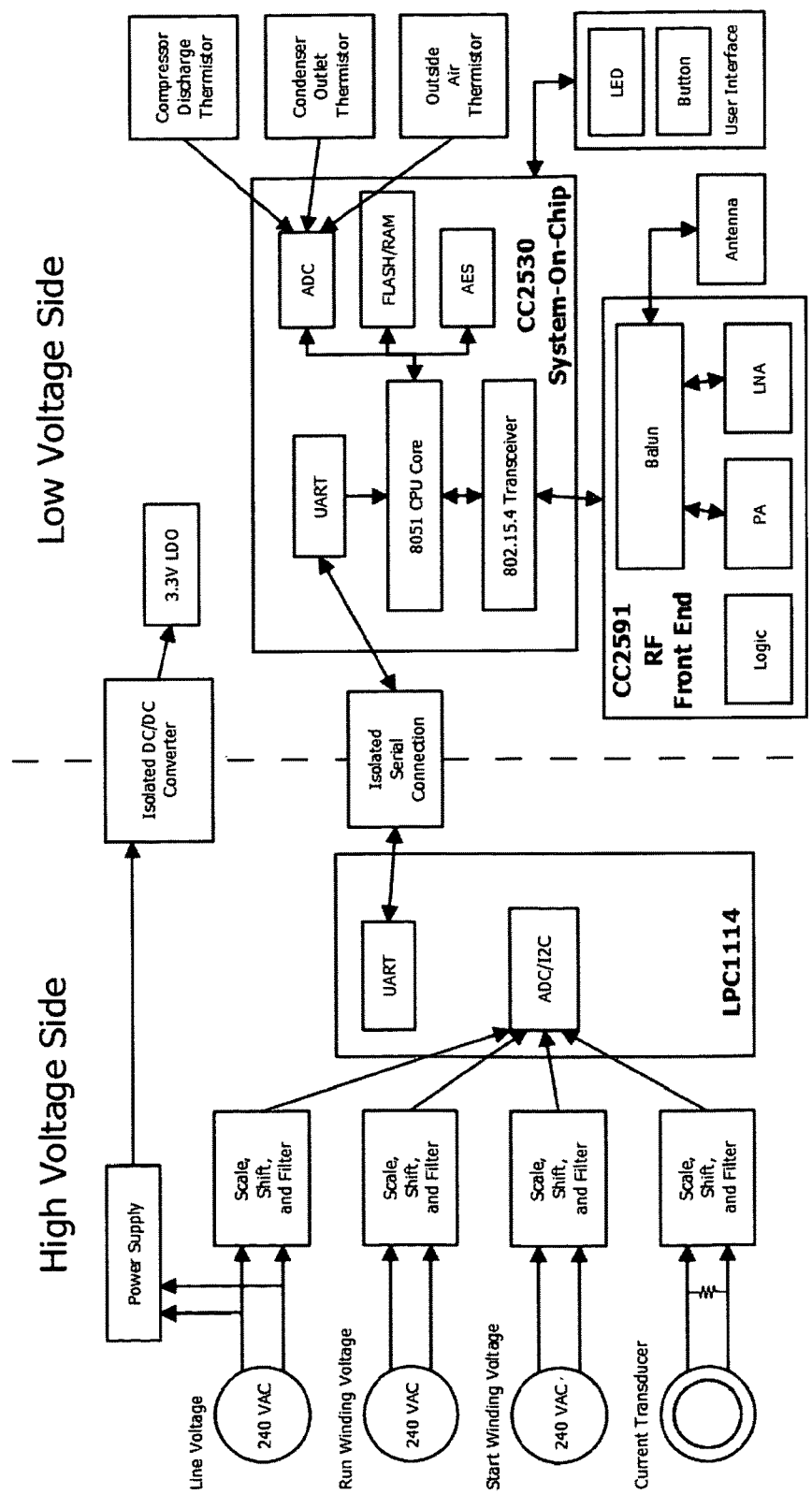
Figure 4: Basic high-level diagram for one embodiment of the OCU-ED

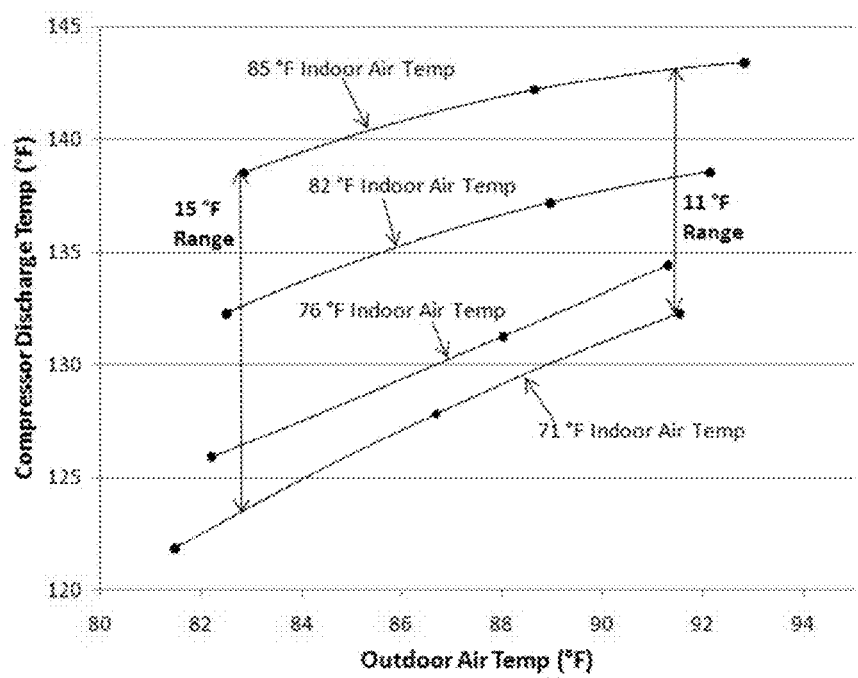
Figure 5: Range of refrigerant temperature at compressor discharge for a properly working A/C unit over a range of indoor air temperature

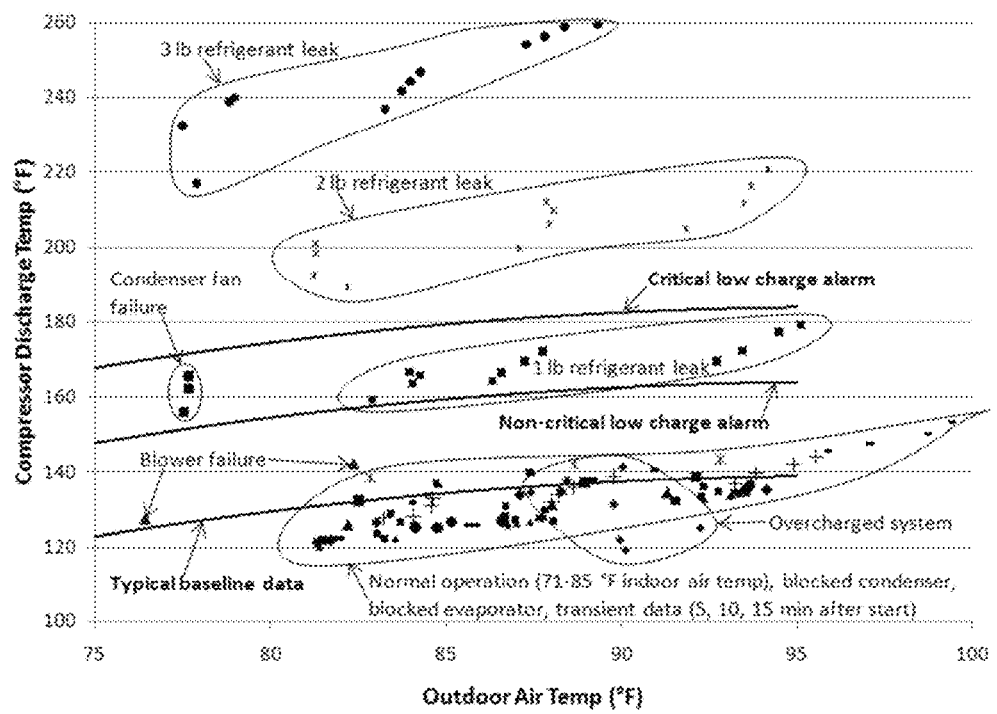
Figure 6: Refrigerant temperature at the compressor discharge under normal and failed conditions described in Table 1

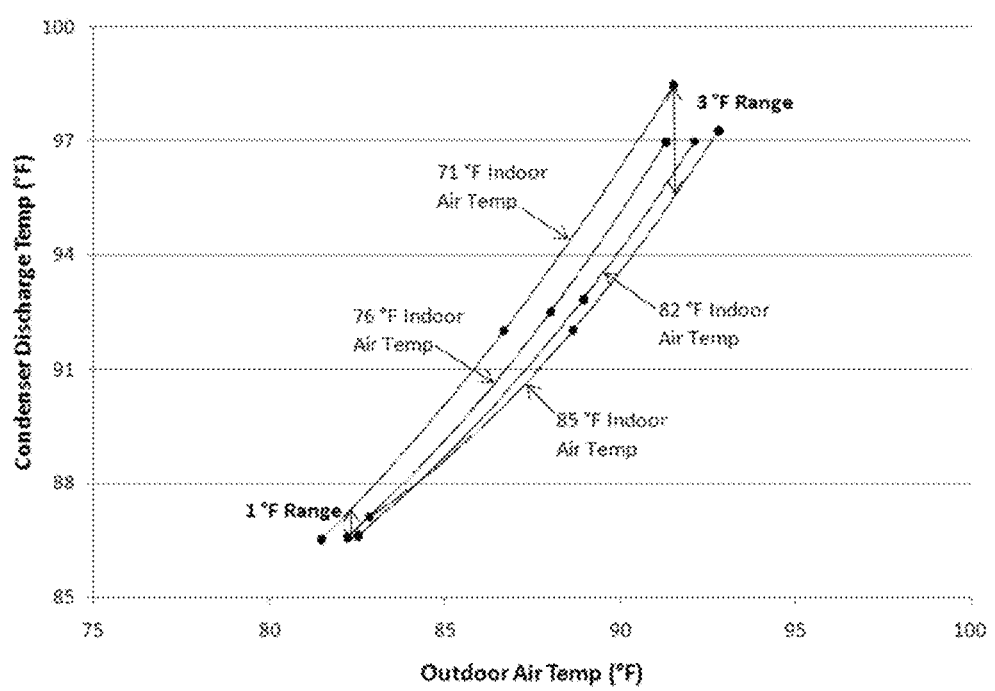
Figure 7: Condenser outlet refrigeration temperature variation with outdoor and indoor air temperature changes under normal A/C unit operation

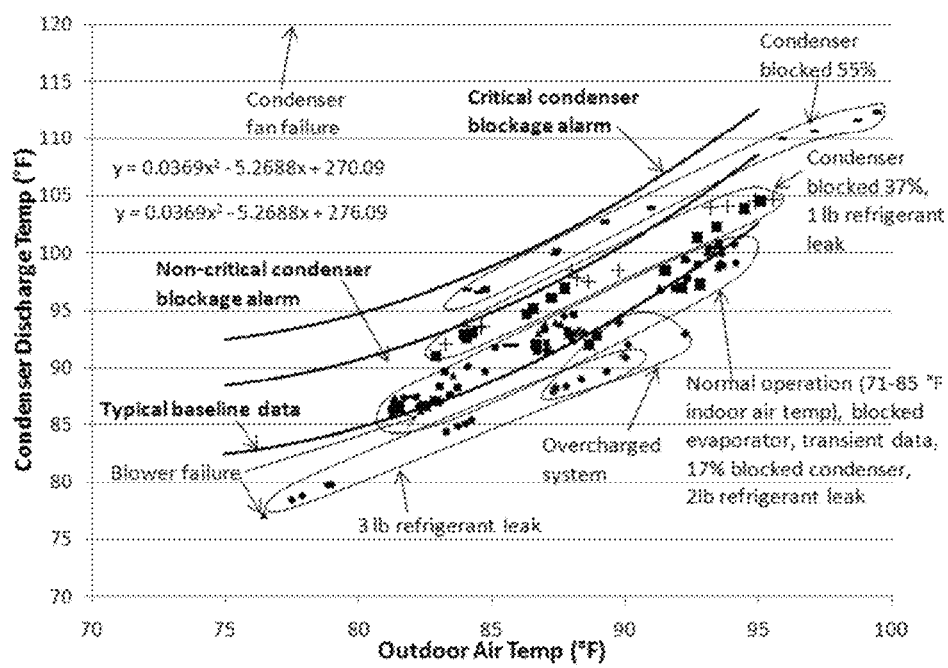
Figure 8: Refrigerant temperature at the condenser outlet as a function of outdoor air temperature for normal and failed situations described in Table 1

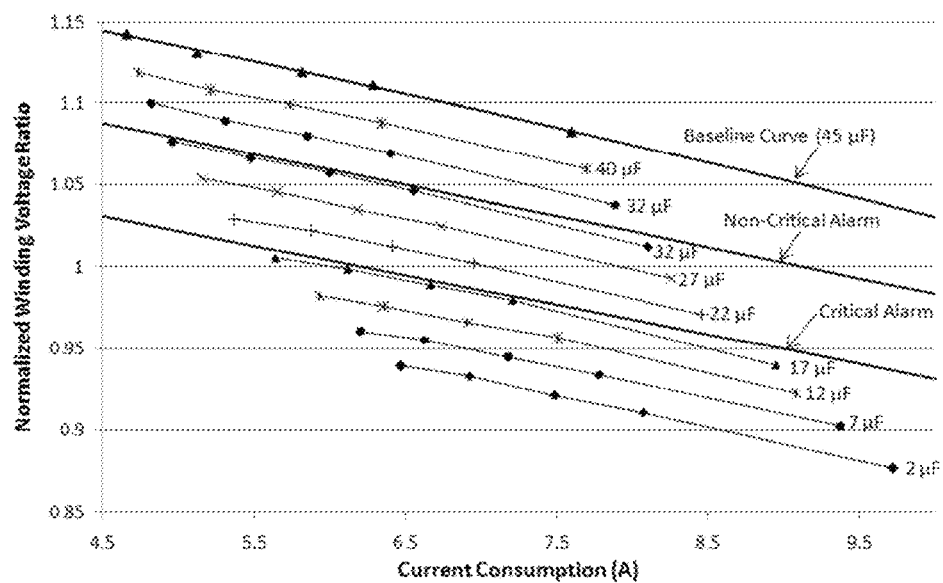
Figure 9: Winding voltage ratio (start winding voltage divided by run winding voltage) as a function of total current used by the condensing unit for various run capacitor values.

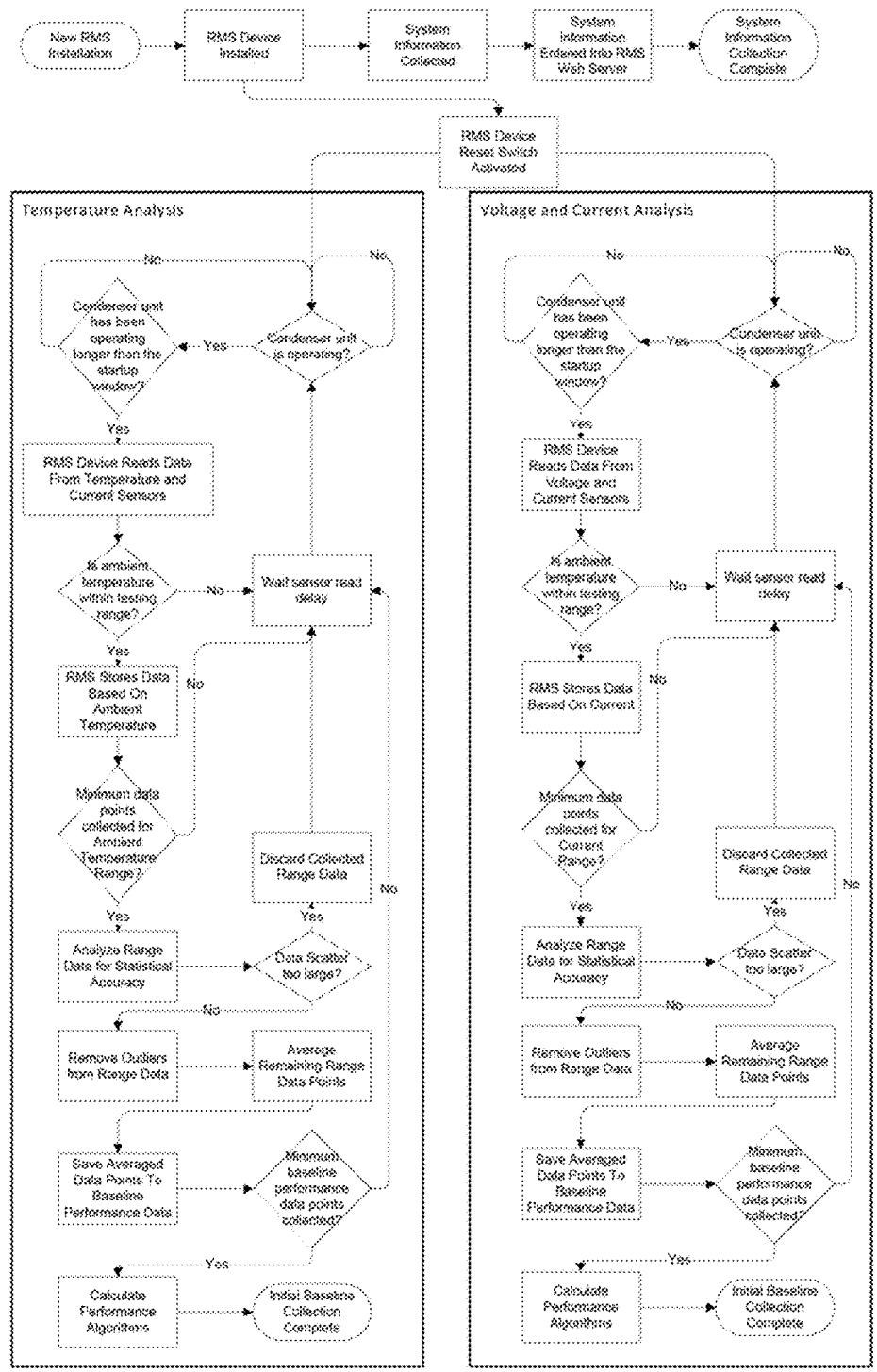
Figure 10: Steps to collect the baseline data (currently preferred embodiment).

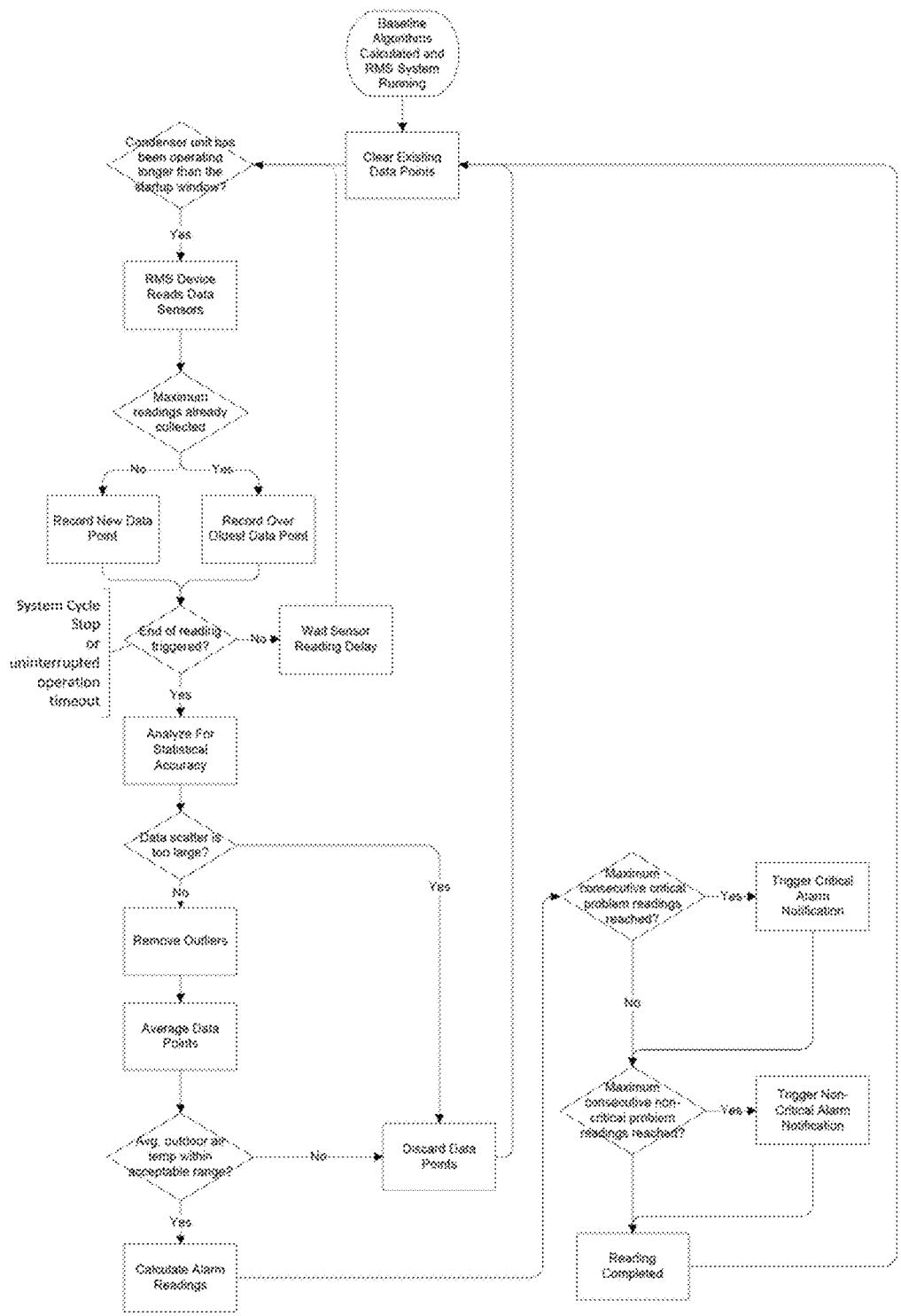
Figure 11: Current preferred approach to compare the measured data with the baseline

WEB-BASED, PLUG AND PLAY WIRELESS REMOTE MONITORING DIAGNOSTIC AND SYSTEM HEALTH PREDICTION SYSTEM

BACKGROUND AND SUMMARY OF THE INVENTION

The following terms and their acronyms are used hereinafter in the description of the invention:

Quality—the ratio of the mass of vapor to the total mass of a saturated substance (see G. Van Wylen and R. Sonntag, Fundamentals of Classical Thermodynamics, p. 37, (John Wiley & Sons, 2nd ed., SI version 1978)).

Flow Quality—the ratio of the vapor mass flow rate to the total mass flow rate.

Access Point (AP)—The device connected to the Internet to transmit data between the Internet and any ED.

End Device (ED)—Any control or monitoring device located remotely from the AP, which sends data or receives commands from the AP.

OCU-ED—An Outdoor Condensing Unit End Device and sensors which monitor performance of a split air-conditioning or heat pump thermal control system.

IAH-ED—An Indoor Air Handler Unit End Device and associated sensors which monitors interior air temperature, and also can monitor performance of the split air conditioner or heat pump thermal control unit.

DHW-ED—A Domestic Hot Water Heater End Device and associated sensors and relays which can monitor and control the hot water temperature being supplied or stored in the hot water tank.

Remote Monitoring System (RMS)—The AP and any ED that communicates with the AP.

Temperature Learning Range—In the currently preferred embodiment, a range of at least 15° F. that will typically occur between 70° F. and 95° F. For example, a data set with data points collected at one degree increments from 72° F. to 87° F. meets the criteria of the Temperature Learning Range.

The most basic vapor-compression refrigeration system consists of four major components: compressor, evaporator, condenser, and expansion device. Actual practical hardware contains many other critical components for reliable, trouble-free operation, such as a control system, high-pressure and low-pressure safety controls, liquid receiver, accumulator, oil separator, crankcase pressure regulator, etc., but the four basic components are all that is needed to illustrate the function of the basic system and the proposed improvement.

In a typical vapor compression system, refrigerant provides a cooling effect as it evaporates, that is, as it boils and turns from liquid to vapor. For pure refrigerants and azeotropic mixtures, if the refrigerant evaporates at a constant pressure, then evaporation occurs at a constant temperature while both liquid and vapor are present. Likewise, refrigerant rejects energy as it condenses from vapor to liquid. For pure refrigerants and azeotropic mixtures, if the condensation occurs at a constant pressure, then the condensation will occur at a constant temperature until all the vapor has condensed to a liquid. Therefore, for evaporation or condensation, the temperature and pressure are related by what is known as the pressure/temperature saturation curve.

In the conventional basic vapor compression cycle shown schematically in FIG. 1, subcooled liquid refrigerant 111 leaves the condenser 112 at high pressure and flows to the throttling device 113 (capillary tube, TXV, etc.) where the pressure is decreased. The refrigerant then enters the evaporator 114 as a two-phase mixture (liquid and vapor) and evaporates or boils at low temperature, thereby absorbing heat. Superheated refrigerant vapor 115 exits the evaporator and enters an electrically-driven compressor 116 where the pressure and temperature are increased as the compressor compresses the refrigerant vapor. The refrigerant vapor leaving the compressor 117 is superheated, and this refrigerant is cooled and condensed in the condenser 112 where heat is rejected, and the refrigerant is condensed to liquid. Refrigerant typically leaves the evaporator 114 slightly superheated (superheat vapor) to assure evaporation has been complete. Refrigerant typically leaves the condenser 112 slightly subcooled (subcooled liquid) to assure condensation has been completed.

FIG. 2 schematically shows vapor compression system that is known as a "split" air conditioning system which is well known in the art. It includes an outdoor unit 20, also referred to as a condensing unit, and an indoor unit 40, also referred to as the fan coil unit or indoor air handler, housed in a structure such as a residential home or a commercial building. The outside of the structure is denoted by numeral 37 and the inside of the structure by numeral 38 with the structure's exterior wall being denoted by numeral 39. The indoor (40) and outdoor (20) units are plumbed together via a liquid line 31 and a vapor line 35 in a known way. A third approximately atmospheric pressure condensed water drain line 36, also known as a condensate drain line, carries water 44 that condenses on the evaporator 42 and is captured in the drain pain 45 of the indoor unit 40. This condensate water is then transported to the outside 37 of the structure, typically to be deposited on the ground 26 near the outdoor unit 20 to create moist wet soil 54. The condensate drain line 36 carries the condensed water from inside 38 being cooled by the system to the outside 37 of the structure (typically by gravity assisted flow only), and is typically bundled with the two refrigerant pipes 31,35 along with any control wires connecting the controls of the indoor and outdoor unit (not shown).

The split system outdoor unit 20 typically includes a compressor 22, condensing coil 23, and cooling fan/motor unit 24 as well as other components well known in the art and is typically located on a concrete or plastic slab or foundation 25 that rests on the ground 26. Standard operation during the cooling season consists of superheated refrigerant vapor entering the condensing unit 20 via the vapor refrigerant line 35. The flow path consists of passing through the compressor 22 and condenser 23, and exiting the outdoor unit 20 via liquid refrigerant conduit 31 and flowing to the indoor unit 40. The cooling fan/motor 24 provides air flow across the condenser. The indoor unit consists of a throttling device 41 (such as a thermal expansion device, orifice plate or capillary tube), evaporator 42 and blower 43 as well as other components well known in the art. Subcooled liquid refrigerant enters the indoor unit 40, flowing to the expansion throttling device 41 and then the evaporator 42 and normally exiting the evaporator as superheated refrigerant vapor flowing back to the inlet of the compressor 22 (which is located in the outdoor unit 20) through vapor refrigerant line 35. Condensate, i.e. condensed water 44, flows by gravity (or by being pumped) in the condensate drain line 36 and exits onto the ground 26 in a region near the outdoor unit 10. Those skilled in the art will understand the foregoing is only a very brief discussion of the operation of a split vapor compression air conditioning system for purpose of defining the condensing unit 20 and the purpose of the liquid line 31, compressor 22, vapor line 35, condenser 23, expansion device 41 and the evaporator 44 in such a system.

It is also well known in the art to use a reversing valve in the outdoor unit 20 along with check valves and two expansion valves to configure the vapor compression system into a device that provides both cooling during warm ambient temperatures and heating during cold ambient periods. Such a vapor compression system, with a reversing valve, is commonly referred to as a heat pump. For both a split air conditioning unit and a split heat pump there are two refrigerant lines connecting the units, one containing condensed liquid refrigerant the other containing vapor refrigerant. In both cases, refrigerant vapor exiting the evaporator flows to the compressor inlet and condensed refrigerant leaving the condenser flows to the throttling valve then on to the evaporator as more simply depicted in FIG. 1.

In a typical residential home, one of the largest sources of energy consumption is the split vapor-compression air conditioning or heat pump system described above (also hereafter referred to as the A/C unit). If the A/C unit is operating at degraded efficiency, an equipment owner may be unaware of the inefficiency because the equipment operates at a higher duty cycle to maintain the house at the appropriate temperature. Eventually, an undetected equipment problem might lead to a costly system failure, such as a compressor motor burnout, or simply lead to increased energy consumption, and failure to cool living spaces adequately during the next hot day.

A/C units that fail on the first unseasonably hot day of the year have typically been operating at reduced capacity (at high duty cycles) for weeks or months. Although the energy bill is higher due to this degraded performance, equipment owners either fail to notice the energy increase or fail to relate the high energy bill to the A/C unit's degraded efficiency. An RMS that can detect degraded A/C unit performance prior to equipment damage or long periods of inefficient operation has obvious benefits to the equipment owner, electric utility, and the environment if such a unit is economical and reliable.

The HVAC service provider also benefits from an RMS by distributing service calls more evenly. Currently, when the first hot days arrive and the unit's degraded capacity becomes apparent, the equipment owner will call a HVAC technician to service the A/C unit. However, the service provider is usually overwhelmed with similar calls on the first hot day where system degradation becomes obvious. For the large service contractor firms with tens of thousands of service contracts, an RMS that can predict failures before they occur or determine inefficient operation has important benefits. The RMS also assists in the scheduling of service calls by providing detailed information regarding the severity of the problem and by offering remote diagnosis. This allows the service provider to dispatch the appropriate repair technician to the site and cluster similar service calls to a technician specialized in that repair.

There are many complex monitoring system approaches, such as the one disclosed in U.S. Pat. No. 7,469,546 that includes the use of temperature, pressure and flow sensors. Using pressure and flow sensors dramatically increases the cost of the monitoring system and makes this type of monitoring system unfeasible for residential or small commercial A/C units. A cost-effective RMS for residential or small commercial A/C units must eliminate expensive sensors and the labor-intensive process of plumbing the sensors into the refrigeration flow circuit. Flow meters and pressure transducers with sufficient accuracies that are included with the complex monitoring system are too expensive for this application. To reduce costs to practical levels, the temperature sensors that directly measure refrigerant temperatures (by being plumbed directly into the refrigerant flow loop) must also be replaced by exterior, surface mount temperature sensors. The in-loop temperature sensors are significantly more expensive than surface mount sensors due to the increased cost of a refrigerant-compatible and pressure-tolerant sensor and the additional cost to install these temperature sensors into the refrigeration flow circuit.

In addition, for the typical split A/C unit or heat pump system, where the evaporator and blower are located inside the conditioned building (and referred to as the air handler or evaporator section) and the condenser and compressor are located outside the conditioned space (and referred to as the condensing unit), it is more difficult to monitor refrigerant pressures, temperatures or flow rates on both the evaporator section and the condenser unit locations since they are not collocated.

U.S. Pat. No. 6,385,510 discusses a remote monitoring method where the conditioned air return temperature and return air humidity, along with the supply air temperature and the system's design airflow rate and rated cooling capacity are used to monitor performance. Using the system's designed airflow rate can, however, introduce a significant amount of error as the air handler airflow rate is a function of the pressure differential across the blower. The geometry, length, or circuiting of the air supply and return ducting will not be identical at all installations, altering the pressure differential across the blower and, therefore, the blower airflow rate. An even larger inaccuracy could be created by the air filter, where there is a wide assortment of air filters that impose different pressure drops and where pressure drop across a filter will change over time due to the filter collecting particles. If the air filter has become significantly clogged, the air handler airflow rate decreases and then this monitoring system would think that cooling capacity was enhanced due to the higher air enthalpy change when, in reality, cooling capacity has been diminished by a clogged air filter.

It is also well known in the art to have a server that is capable of communicating with one or more remote locations, to send and receive data from these remote units for the purpose of monitoring or controlling multiple devices. For example, U.S. Pat. No. 7,792,256 discloses a system for remotely monitoring, controlling, and managing one or more remote premises.

We have discovered that there is a far more cost-effective way to do remote monitoring using compressor discharge sampling without sacrificing accuracy in predicting the health of the system being monitored. In order to appreciate just how significant our discovery is, however, some additional background discussion is useful.

It well known to those skilled in the art that when a fluid, such as refrigerant in the evaporator of a vapor compression system of the types shown in FIGS. 1 and 2, evaporates, that refrigerant does so at a constant temperature as long as the pressure is constant, From a mathematical perspective, the evaporating pressure and evaporating temperature are related and not independent. That is, for a specific refrigerant, if the evaporating pressure is known, then the evaporating temperature can be determined by reference to that refrigerant's known saturation pressure temperature relationship which is valid only when the refrigerant is saturated. Once all the refrigerant liquid has evaporated, additional heat input will cause the refrigerant temperature to increase above saturation temperature and the refrigerant is referred to as being superheated. The numerical increase in the temperature of the refrigerant above the saturation temperature is referred to as the superheat of the refrigerant. That is the mathematical difference between the actual temperature and the saturation temperature (at that pressure) is the superheat of the refrigerant.

For example, using the NIST Standard Reference Database 23, version 8.0 software program titled REFPROP, available from the US Department of Commerce; the saturation temperature of Refrigerant 134a at 40 psia is 29 degrees F. If the refrigerant has been heated to 34 degrees F., (and the pressure held at 40 psia) then the superheat would be 5 degrees F.

Therefore, we recognized when examining the condition of the refrigerant exiting the evaporator, with only a temperature sensor, the diagnostic value of the knowing both the temperature and pressure at this exit can be undesirably limited. If the temperature is above the saturation temperature, as in the case just discussed when the refrigerant is superheated, then the exit enthalpy, or similarly the thermodynamic state point, can be determined. However, if the temperature exiting the evaporator is the saturation temperature (for the measured pressure), then it is not possible to determine the flow quality from only these two measurements. That it, is not possible to determine if the refrigerant flowing from the evaporator outlet is nearly all liquid, nearly all vapor, or some other saturated condition. Without this knowledge of the flow quality, the thermodynamic state point or the exit enthalpy of the saturated refrigerant exiting the evaporator outlet cannot be determined. This also means the effectiveness of the evaporator at evaporating the entire refrigerant, cannot be determined with only the exit pressure and temperature measurements, if refrigerant is leaving the evaporator in a saturated condition. It is for this reason, that thermal expansion valves and other feedback expansion devices are necessary to monitor exit superheat, and the evaporators of these systems are designed to have superheated refrigerant exit the evaporator. This exit superheat is typically very small, since the primary function of the evaporator is to vaporize refrigerant. Under certain fault conditions, the superheat may be excessive, such as when the refrigerant charge is low, in other cases the superheat may be negligible or the evaporator exit may be saturated. When the refrigerant exits the evaporator as a saturated refrigerant, it is not possible to determine the quality that is the relative amount of vapor and liquid refrigerant exiting the evaporator; hence, it is also not possible to determine how much the cooling capacity of the evaporator has been degraded.

The foregoing point is most easily demonstrated by the following example. For a unit mass of refrigerant, the heat absorbed by evaporation, i.e., the heat of vaporization is much greater that the heat capacity of a single phase superheated refrigerant. In the case, for example, of abovementioned Refrigerant 134a and using REFPROP once again, the energy to evaporate one pound of Refrigerant 134a from saturated liquid to saturated vapor (at a saturation pressure of 40 psia, saturation temperature of 29 degrees F.), namely the latent heat of vaporization is 86.0 BTU/LB, whereas the energy to raise the temperature of the refrigerant from the saturation temperature of 29 degrees F. to 34 degrees (5 degrees F. of superheat) is only 1.1 BTU/LB or only 1.3% of the latent heat of vaporization (1.1/86). Likewise, the energy to raise the temperature of the refrigerant from the saturation temperature of 29 degrees F. to 39 degrees (10 degrees F. of superheat) is only 2.1 BTU/LB or 2.4% (2.1/86). Therefore if the cooling provided by evaporation increased by about 1% (energy into the evaporator increased by 1%) the superheat would increase from 5 degrees F. to about 10 degrees F., and therefore this increase could be easily determined by a noticeable temperature change of 5 degrees F.

If, however, the cooling provided by evaporation decreased by anything more than about 1% (energy into the evaporator decreased by more than 1%) there would be no superheat at the exit; rather the refrigerant would be leaving the evaporator at saturated conditions, in the case of this example, 29 degrees F. The two important points to be made here are (1) by simply monitoring the temperature in the conventional way it is not possible to determine if the cooling (namely the evaporation in the evaporator) has decreased by 1% or 90%, since the refrigerant exiting the system would be saturated and therefore at the same temperature, and (2) a very accurate measurement of the temperature at the outlet of the evaporator is necessary if one has any hope of determining any reduction in cooling capacity, since a 5 degree reduction in outlet temperature is only a 1% reduction in capacity and, once saturated outlet conditions are achieved, no further temperature measurements are useful.

We have discovered an inexpensive diagnostic method that makes it possible to identify reductions in cooling before they become significant and to provide this diagnostic warning at minimal cost. To reduce cost, all measurements are collected at a single location, namely the condensing unit, without the need to install sensors inside the structure being cooled or on the indoor air handling unit. While our method could measure the refrigerant temperature at the inlet to the compressor, which represents the first component downstream of the outlet of the evaporator, or measure the temperature anywhere in the refrigerant line between the evaporator outlet and the compressor inlet, we recognized that even small heat transfer with the ambient could affect an accurate reading of the superheat temperature and if incomplete evaporation were occurring, the same inability to determine the flow quality, with only a temperature measurement would still be present.

We have discovered another and far superior method of determining a reduction in the evaporation at the outlet of the evaporator that only relies on a temperature measurement, but can still determine the relative amount of saturated vapor, that is the relative quality, exiting the evaporator. Since, as we recognized, the compressor normally inputs a relative constant amount of energy into the refrigerant (for a specific outdoor air temperature), and the refrigerant always exits the compressor as a superheated vapor, by investigating the temperature at the outlet of the compressor, that is by looking at the compressor discharge temperature, the relative amount of evaporation in the evaporator can be easily determined. If the refrigerant exits the evaporator with a low thermodynamic flow quality, meaning a large fraction of saturated liquid is leaving the evaporator, the temperature at the outlet of the compressor will be lower. Likewise if the refrigerant exits the evaporator with a high thermodynamic flow quality, meaning a small fraction of saturated liquid is leaving the evaporator, the temperature rise at the outlet of the compressor will be far greater, and if the refrigerant exits the evaporator as a superheated vapor, the temperature rise at the outlet of the compressor will be even more. Once again an example from REFPROP may be useful.

If 1 pound per hour of R-134a refrigerant (at 40 psia) leaves the evaporator with a quality of 0.5 (half vapor by mass) which represents an exit enthalpy of 128.1 BTU/lb and has the compressor input 60 BTU/hr of energy into the system, the refrigerant will be discharged from the compressor with an enthalpy of 188.1 BTU/Lb. If the pressure at the compressor discharge is 140 psia, then the refrigerant is discharging the compressor at a temperature of 131.6 degrees F.

Alternatively, if 1 pound per hour of R-134a refrigerant (at 40 psia) leaves the evaporator with a quality of 0.9 (90% vapor by mass), which represents an exit enthalpy of 162.5 BTU/lb and has the same compressor energy input of 60 BTU/hr into the system, the refrigerant will discharge the compressor with an enthalpy of 222.5 BTU/Lb. If the pressure at the compressor discharge is again 140 psia, then the refrigerant is now being discharged from the compressor at a temperature of 269.5 degrees F. A 137.9 degree F. increase occurs due to the quality change from 0.5 to 0.9.

Finally, if 1 pound per hour of R-134a refrigerant (at 40 psia) leaves the evaporator with a superheat of 5 degrees F. (exit temperature of 34 degrees F. and pressure of 40 psia), which represents an exit enthalpy of 172.1 BTU/lb and has the compressor inputs the same 60 BTU/hr of energy into the system, the refrigerant will be discharged from the compressor with an enthalpy of 232.1 BTU/lb. If the pressure at the compressor discharge is again 140 psia, then the refrigerant is now being discharged from the compressor at a temperature of 306 degrees F. A 36.5 degree F. increase due to a change from a saturated at a quality of 0.9 to superheated 5 degrees F.

As the foregoing example clearly demonstrates, by measuring the temperature at the compressor discharge, rather than the evaporator inlet, the effects of different evaporator exit conditions, is greatly amplified. This simplifies the measurement and less accurate temperature measurements on the exterior of the tube can be used since the temperature differences are much larger than the typical 5 degree F. variation at the evaporator outlet (between superheated evaporator discharge and a saturated discharge). Also by measuring the temperature at the compressor discharge, different evaporator exit qualities, i.e., different levels of evaporation can also be determined from the corresponding compressor discharge temperature.

Hence, one object of the present invention is to provide a reliable, low-cost vapor-compression air-conditioning and heat pump monitoring system that can reliably predict equipment failures and determine low-efficiency operation. This monitoring system can be located entirely in the outdoor condensing unit, without the need to place any sensors inside the building or inside the indoor portion of the split air conditioning or heat pump unit. This greatly simplifies installation and lowers cost.

The present invention disclosed herein utilizes only three temperature sensors, a current sensor, and three voltage sensors. Two of the temperature sensors are mounted on the exterior surfaces of pipes located in the outdoor condensing unit, while the last temperature sensor measures outdoor air temperature. The tube-mounted temperature sensors are located on the compressor discharge tube and the condenser outlet tube. The current draw of the compressor or the total current to the condensing unit, which includes the power to both the compressor and the condenser fan, is also measured to identify potential problems. Two voltage measurements (Run Winding Voltage, Start Winding Voltage), are also used. Optionally, the inlet voltage can also be measured, to verify the status of the condensing unit's contactor (relay). With this information, the system, according to the present invention, can automatically learn the characteristics of the specific vapor compression system, then monitor the system for future problems, including faulty run or start capacitance operation, low refrigerant charge, reduced condenser airflow or reduced evaporator airflow. In addition to split air conditioning or heat pump systems, this same diagnostic approach can be applied to any vapor-compression system, including refrigerators, freezers and the like.

We have developed a family of novel diagnostic algorithms to enable the identification of all common mechanical problems, electrical problems, and maintenance issues. These algorithms have been designed to be very simple, thereby allowing the analysis to be performed on site or at a remote location, by transferring the data via the internet or other means, or by using a combination of both on-site and remote analysis to allow reduced data traffic, safe storage of the data, and reduced server loading.

In one currently preferred embodiment, the system consists of an indoor AP device which provides communication between the OCU-ED and the server computer, located at a remote location and connected via the Internet or other appropriate communications system. The OCU-ED can be installed quickly on the condensing unit without any modifications to the plumbing or condensing unit since measurements are obtained on external tube surfaces in the outdoor condensing unit, the ambient outdoor air, from voltage measurements from capacitors and contactor connection surfaces in the outdoor unit, or from current draw of a compressor or overall outdoor condensing unit power supply conductor either of which is routed through a current sensor.

The AP device of the present invention would also allow additional end devices to be located in the building. For example, a second end device, referred to here as the IAH-ED, could be used to monitor the indoor air temperature returning to the air handler and can therefore provide a thermostatic like thermal control effect, to override the existing thermostat and provide precise temperature control based on instructions from the AP. That is, a programmable thermostatic effect, selected via the Web-based interface and transmitted by the AP to this end device, could be used to control the room air temperature. Likewise, one skilled in the art could extend this invention to other items in the home, such as for example a DHW-ED, which along with associated sensor and relay, can monitor and control the domestic hot water supply temperature based on instructions from the AP. That is a programmable time-dependent thermostatically-controlled hot water heater effect, selected via the Web-based interface and transmitted by the AP to this DHW-ED, could be used to monitor and control the domestic hot water supply temperature.

BRIEF DESCRIPTION OF THE DRAWINGS

These and other objects, features and advantages of the present invention will become more readily apparent from the following detailed description when taken in conjunction with the accompanying drawings wherein:

FIG. 1 is a highly simplified schematic diagram of the conventional electrically-powered vapor compression unit described above.

FIG. 2 is a schematic view of the known vapor compression split A/C unit described above.

FIG. 3 is a schematic diagram showing information flow in the currently preferred embodiment described in detail herein below.

FIG. 4 is a basic high-level diagram of one currently contemplated embodiment of the OCU-ED in connection with the present invention.

FIG. 5 is a graph which displays the variation of refrigerant temperature at the compressor discharge for a range of indoor and outdoor air temperatures of a properly operating A/C unit.

FIG. 6 is a graph which shows an example of identifying low refrigerant charge using the compressor discharge temperature by comparing the measured value to the baseline curve of various system faults.

FIG. 7 is a graph which displays the variation of refrigerant temperature at the condenser outlet for a range of indoor and outdoor air temperatures of a properly operating A/C unit FIG. 8 is a graph which shows an example of identifying low condenser airflow using the condenser outlet (liquid line) refrigerant temperature by comparing the measured value to the baseline curve of various system faults.

FIG. 9 is a graph which shows the variation of winding voltage ratio to current at normal and degraded run capacitor capacitances for a condensing unit.

FIG. 10 is a flow chart which shows steps to collect the baseline data for the currently preferred embodiment.

FIG. 11 is a flow chart which shows the current preferred method to compare the measured data with the baseline performance curves.

DETAILED DESCRIPTION OF THE DRAWINGS

A basic RMS consists of a minimum of two components: the OCU-ED installed on the outdoor condensing unit of a typical residential (or small commercial) split A/C or heat pump system (or a unitary system) and the AP providing a bi-directional communications link. The AP is an Internet bridge that communicates with any remote device in the home (such as the OCU-ED) and transmits the communication via the Internet to a web-based monitoring site. The OCU-ED performs A/C unit data collection and some on-site analysis. This collected data is then transmitted to the AP and sent to the web-based server for data processing, storage, and analysis.

The OCU-ED of the RMS system is designed to monitor A/C unit parameters daily and provide early detection of maintenance issues (dirty condenser coil, dirty air filter, etc.) and service repair issues (such as low refrigerant charge, failed run or start capacitor, faulty fans or blowers, short cycling, etc.). When a problem is detected, the system will automatically notify the equipment owner and the HVAC service and repair company (hereafter referred to as the repair service provider) that installed the RMS.

The AP gateway serves as a pass-through for data and will be configured to collect the data from the remote devices and pass it to the central server via standard Internet protocols.

FIG. 3 shows a currently preferred embodiment of the overall system communication and the basic information flow. This type of architecture is particularly preferred in the field because it allows for scalability for structures with multiple A/C units or additional end devices. The system takes advantage of wireless mesh networking to pass messages between end devices and the access point even when the origin and destination are not within transmitting reach of each other. End devices are able to directly query each other to determine operating parameters, sensor readings, and other information determined to be relevant by an ED.

FIG. 4 shows the currently preferred embodiment of the Outdoor Condensing Unit End Device (OCU-ED). The OCU-ED electronics are separated into two sides, one for high voltage signals and the other for low voltage signals. The two sides are galvanically isolated to reduce shock risk to users. On the high voltage side there is the analog portion, a microcontroller and the power supply. The analog portion monitors 3 high voltage signals and one current signal fed to a burden resistor from a current transformer. These signals are scaled and shifted from AC signals to low voltage DC signals using a differential amplifier circuit. The signal is then filtered with a low pass filter and sent to the microcontroller's analog to digital converters for analysis.

The microcontroller reads each signal at multiple kilohertz with its analog to digital converter. The original signal values are then extracted from the results of the analog to digital converter using previously determined calibration data. The original signal values are sent to the low side through an isolated serial connection to be analyzed.

The power supply is powered off the line voltage supplied to the condensing unit and the power takeoff is located upstream of the contactor which closes to power the compressor so that this circuit is always hot. The power supply provides low voltage DC power to each side of the board.

On the low voltage side is a wireless transceiver microcontroller, an RF front end IC, antenna, thermistor inputs and user interface components.

The wireless transceiver microcontroller used in the preferred embodiment is the CC2530. Connected to the Radio of the CC2530 is the RF front end IC. This IC increases transmitter power and receiver sensitivity to increase the communication range. The CC2591 is used for the RF front end. Connected to the CC2591 is a PCB mount antenna.

Negative temperature coefficient thermistors are connected to the microcontroller's analog to digital converter through a voltage divider and a low pass filter. LED light signals are used to provide basic status information to the user. A button is also connected to the microcontroller to give the user basic control.

Algorithms were developed to detect performance degradation in a vapor compression system using a minimum of only three temperature measurements, three voltage readings, and a current measurement. As a result, no pressure transducers or flow meters are required for accurate monitoring. Eliminating pressure transducers was essential because they can become a source of refrigerant leaks (due to vibration, under-tightening, or over-tightening), and are cost prohibitive. Additionally, pressure transducers exhibit calibration drift over time, with decreasing monitoring accuracy. The temperature measurements being used in this invention can employ inexpensive, rugged thermistors, or similar low cost temperature sensors, which in the case of thermistors change resistance with temperature and therefore are subject to negligible calibration drift.

Other inexpensive temperature sensors can be used and is well known in the sensing art. The current transducer and voltage sensors are also inexpensive and very reliable. Since performance degradation or failure prediction is determined by a change in performance over time, sensor repeatability is critical. Sensors need not be calibrated to specific absolute values. The temperature sensors need only be located on the external surfaces of the refrigerant tubing, rather than directly in contact with the refrigerant, and their exact placement on the compressor discharge tube or condenser outlet tube is not critical, as long as they are near enough to these devices to provide proper measurements without being affected by external factors such as sunlight.

In our currently preferred embodiment, sensor data obtained by the OCU-ED is processed locally to determine general A/C unit performance characteristics and uploaded to a web server where more detailed analysis can be optionally performed. The frequency of the upload is determined from the results of the local OCU-ED data analysis. In the current embodiment, the minimum upload frequency is once per day, and the maximum upload frequency is once every time the unit cycles off (or every hour if it operates for more than 1 hour continuously). Systems operating near alarm values upload data more frequently. The RMS methodology requires collecting baseline data immediately after installation or tune-up servicing by an HVAC professional (when the system is assumed to be operating properly). The OCU-ED collects baseline data and automatically calculates a performance model that describes proper performance as a function of outdoor air temperature for that individual A/C unit. A complete set of baseline data includes: (1) a curve of compressor discharge temperatures (on the external surface of the tubing) verses outdoor air temperature, developed from data collected while operating within the outdoor Temperature Learning Range, (2) a curve of condenser outlet (liquid line) temperature (on the external surface of the tubing) verses outdoor air temperature developed from data collected while operating within the outdoor Temperature Learning Range, (3) a curve of compressor, or condensing unit, current draw verses outdoor air temperature, developed from data collected while operating within the outdoor Temperature Learning Range, and (4) a curve of start winding voltage divided by run winding voltage (or the inverse) verses total current, developed from data collected while operating within the outdoor Temperature Learning Range.

After a complete set of baseline data is collected, a family of equations to define normal operation is developed and used to compare against all future measured data. System alarms are triggered when data points consistently fall outside of the acceptable range of operation. This methodology has been tested and demonstrated to successfully learn the A/C unit characteristics and subsequently monitor future performance. Details of this algorithm and the results of experiments are set forth below.

Typical failure modes that occur in a residential or small commercial A/C unit include:

1. Loss of Refrigerant Charge—An A/C unit with a slow leak can operate inefficiently for months or years before it is incapable of maintaining the desired indoor air temperature on a very hot day. Before this A/C unit failure, the loss of cooling capacity is masked by higher A/C unit duty cycle and additional energy consumption. Unfortunately, by the time the capacity and efficiency degradation is typically identified by the equipment owner, the system has been wasting energy for months, if not years. In addition, if a refrigerant leak is not identified prior to a significant loss of refrigerant, a complete failure (compressor failure) or iced-up evaporator can occur, resulting in a total loss of cooling capacity and potentially significant damage to the A/C unit or home (mold growth).

2. Degraded Run Capacitor—The capacitance of the Run Capacitor typically diminishes over time due to various factors, such as leaking electrolyte or reduced foil capacitance. This degradation cannot be identified visually since no physical evidence of electrolyte leaking is visible. This decrease in capacitance reduces the starting torque developed by the compressor's motor, and at some point the compressor will no longer start. This failure often occurs on the first hot day of the year as the required starting torque increases with outside air temperature. Once again, these symptoms are unknown to the equipment owner until the compressor will not start on one of the hottest days of the year.

3. Faulty Potential Relay or Degraded Start Capacitor—When included with a system, and working properly, the Start Capacitor is connected to the start winding circuit for milliseconds by the Potential Relay during compressor start-up. This provides increased starting torque to help start the compressor motor. Like a degraded Run Capacitor, a degraded Start Capacitor or a failed Potential Relay will lower the starting torque developed by the compressor's motor. At some point the compressor will no longer start, resulting in total loss of cooling. The starting torque required increases with outside air temperature; this is another problem that has symptoms the equipment owner can't detect until the compressor will not start, likely on one of the hottest days of the year.

4. Blocked or Restricted Condenser Airflow—Low condenser coil airflow can be caused by a dirty condenser coil, overgrown plants around the condensing unit, or the condenser fan blade rubbing on the housing. Low condenser airflow will require the compressor to consume more energy (along with a decrease in A/C cooling capacity) since the condenser saturation temperature must be higher to achieve the same heat rejection. This lowers the performance of the unit, accelerates damaging acid formation, and shortens the life of the A/C unit (from both an acid and mechanical degradation standpoint). Additionally, reduced condenser airflow could reduce the life of the condenser fan due to increased motor load and reduced motor cooling airflow. While the equipment owner may be able to detect the noise of a rubbing condenser fan or clearly see an obstructed airflow path, most equipment owners rarely inspect their condensing unit visually.

5. Blocked or Restricted Evaporator Airflow—Slight changes in airflow, which could be caused by a change in air filter type or quality of the filter, are normal and must not be flagged as an alarm. For example, the airflow rate though a MERV 11 pleated filter is far less than the airflow through an expensive MERV 6 fiberglass mat filter, and the equipment owner could switch filter types monthly or seasonally. Significant loss of airflow however, should be identified as a problem.

6. Pitted Contactor—The Contactor is a relay that provides power to the Outdoor Condensing Unit when the thermostat calls for cooling. Pitted electrical contact surfaces on the Contactor make a poor electrical connection, causing electrical resistance and a voltage drop to the electrical components in the condensing unit (compressor and fan). This voltage drop increases current and causes substantial heating of the Contactor's electrical contact surfaces, resulting in further pitting of the Contactor. The reduced voltage caused by the pitted Contactor will lower the voltage to the compressor and blower fan, resulting in lower starting and operating torque to these electric motors, eventually reaching a point where they can no longer operate. In the preferred configuration, the RMS should detect a pitted Contactor.

In order to create these common faults and provide examples of the capability of the disclosed invention herein, a 3-ton A/C unit was placed into an environmental chamber and operated under normal and fault conditions. Table 1 below provides a summary of the common faults created on this system.

TABLE 1

A/C unit o wrating conditions tested

| Test Condition | Air Filter | Condenser | Refrigerant Charge | Indoor Air Temp (° F.) | Outdoor Air Temp (° F.) |
|---|---|---|---|---|---|
| Normal Operation | Clean | Clean | Proper charge | 71-85 | 80-95 |
| Dirty/Blocked Condenser | Clean | 18% blocked | Proper charge | 72-76 | 80-95 |
| Dirty/Blocked Condenser | Clean | 37% blocked | Proper charge | 71-85 | 80-95 |
| Dirty/Blocked Condenser | Clean | 55% blocked | Proper charge | 71-85 | 80-95 |
| Dirty/Blocked Air Filler | 17% Blocked | Clean | Proper charge | 71-73 | 80-95 |
| Dirty/Blocked Air Filter | 37% Blocked | Clean | Proper charge | 73-77 | 80-95 |
| Dirty/Blocked Air Filter | 55% Blocked | Clean | Proper charge | 71-85 | 80-95 |
| Ditty/Blocked Air Filter | 73% Blocked | Clean | Proper charge | 71-85 | 80-95 |
| Low Refrigerant Charge | Clean | Clean | 1 LB low | 71-85 | 80-95 |
| Low Refrigerant Charge | Clean | Clean | 2 LB low | 71-85 | 80-95 |
| Low Refrigerani Charge | Clean | Clean | 3 LB low | 71-85 | 80-95 |
| Refrigerant Overcharged | Clean | Clean | 1 LB high | 79 | 90 |
| Refrigerant Overcharged | Clean | Clean | 2 LB high | 81 | 90 |
| Refrigerant Overcharged | Clean | Clean | 3 LB high | 76-82 | 90-92 |
| Refrigerant Overcharged | Clean | Clean | 4 LB high | 74-82 | 87-90 |

To minimize cost and installation time, we have discovered that the following sensors commonly used in remote monitoring and system diagnostic procedures are not required for accurate health and performance predictions using our approach. The elimination of these sensor data simplifies installation, lowers cost, and improves reliability of the monitoring system.

Indoor air temperatures—While typical remote monitoring devices monitor indoor air temperature (evaporator inlet air temperature) as well as evaporator air exit temperature, we have found that monitoring these temperatures is not necessary for detection of potential faults in the system. Since the currently preferred embodiment for the remote monitoring locates the OCU-ED outside (at the condensing unit), indoor air temperature monitoring and/or evaporator discharge air temperature monitoring would add significant cost to the unit and unnecessary complexity to the installation.

Condenser discharge air temperature—While some remote monitoring devices monitor condenser inlet air temperature, which is the outdoor air temperature, as well as condenser discharge air temperature, we have found that that only outdoor air temperature needs to be measured. We have also discovered that spatial temperature gradients in the condenser air discharge also make the condenser discharge air temperature measurements inaccurate. The use of the additional temperature sensor would also add unneeded cost, inaccuracy, and complexity to the system.

Condenser Refrigerant Inlet and Outlet Temperature—Some remote monitoring devices monitor the enthalpy change of the refrigerant entering and exiting the condenser, or estimate this enthalpy change by measuring the temperature change across the condenser. However, we have discovered a monitoring and fault prediction method that does not require these temperature measurements; rather only the surface temperature of the condenser discharge piping needs to be measured as a function of outdoor temperature. The use of the temperature sensors in the refrigerant flow would likewise add cost and installation complexity.

Evaporator Refrigerant Inlet and Outlet Temperature—Typically, the conventional method of determining low refrigerant charge in a fixed expansion device, such as a capillary tube or orifice plate expansion device, is to measure the evaporator saturation temperature or pressure and evaporator discharge temperature so that evaporator superheat can be determined. Evaporator superheat is also the conventional method of determining a dirty evaporator, clogged air filter, and poorly operating evaporator blower. Evaporator superheat is the difference between evaporator discharge temperature and evaporator saturation temperature. Therefore, conventional monitoring devices typically monitor the temperature of the refrigerant entering and exiting the evaporator; however, we have discovered a monitoring and fault prediction method that does not require these temperature measurements. Once again, the use of the temperature sensors in the refrigerant flow would add cost and installation complexity. In addition, as stated earlier, since the currently preferred embodiment for the remote monitoring is to locate the OCU-ED outside (within the condensing unit), indoor refrigerant temperature monitoring would add significant cost to the unit and complexity to the installation.

Refrigerant temperature at the compressor suction—Although we have discovered that compressor suction temperature is one potential indicator of insufficient charge, we have further discovered that the compressor discharge temperature is dramatically affected by compressor suction temperature, and amplifies the effect. Monitoring the compressor discharge temperature thereby provides a more pronounced indication of system charge effects, and thereby provides for a dramatically improved sensitivity, without the need to dramatically improve the sensitivity and cost of the actual temperature sensor. This amplified affect allows the use of an external temperature measurement on the surface of the compressor discharge tubing rather than requiring a temperature measurement directly in the refrigerant stream.

Compressor can temperature—Typically, a conventional method of determining improper charge or poor evaporator performance has been to monitor the external compressor housing of a hermetic compressor (typically referred to as the compressor can). However, we have discovered that the temperature (at any location on the compressor can) cannot be used in performance monitoring because of significant fluctuations due to the boiling of liquid refrigerant in the compressor housing. The amount of liquid refrigerant in the compressor can housing and the rate at which it evaporates is a function of many variables, some which cannot be accurately measured or known. Refrigerant pressure (high-side and low-side)—Essentially all monitoring of a vapor compression system performance has traditionally relied on the measurement of the refrigerant pressures on the low- and high-sides of the system. For example, the first thing a refrigeration technician is trained to do during a service call is to connect a manifold gauge set to visually inspect the operating pressures. Unfortunately, as stated earlier, this adds significant component cost, installation cost and complexity, and calibration drift. Although these pressures can be used to analyze the system, we have discovered an alternative method that does not require the use of pressure measurements for accurate health monitoring or fault prediction.

The Fault Detection Method of the Present Invention

Failure Mode 1: Low Refrigerant Charge

To detect low refrigerant charge, a baseline curve of compressor discharge temperature (measured on the external surface of the discharge piping to reduce cost) versus outdoor ambient temperature is developed by collecting data during the learning period. After sufficient baseline data has been collected over a range of outdoor air temperatures, a best-fit polynomial is automatically calculated. This baseline best-fit polynomial allows the OCU-ED to calculate the typical compressor discharge temperature for any outdoor air temperature. When the measured compressor discharge temperature is between 25° F. and 45° F. above the predicted value from the baseline curve, then a low-priority warning of low-charge is indicated. If the measured discharge temperature is more than 45° F. above the predicted value from the baseline curve, then a high-priority (imminent failure) warning of low-charge is indicated. It will now be understood by one skilled in the art that a key to this invention is the use of the temperature of the external surface of the refrigerant line at the compressor discharge as an indicator of system problems. The actual variation to be used to detect a problem is dependent on the level of detection desired by the designer. It is also contemplated that compressor inlet temperature could be used instead of compressor discharge temperature; however, we have discovered that the compressor discharge temperature variation is more sensitive to low-charge and will indicate a problem earlier. The relative insensitivity of this configuration to the exact location of sensors, due to the baseline performance being developed after the sensors are located, is the case for all the sensors used in this invention. Of course, normal sensor positioning practices that are well known in the art, must be followed, namely the sensor should be located on the sides of the tube, and should avoid being located at the top or bottom of the tube.

Example 1: Demonstrating the Capability to Identify Low Refrigerant Charge

In addition to decreasing the life of an A/C unit and wasting electrical power by decreasing A/C unit cooling capacity, a low refrigerant charge indicates a leak in the system that is venting a greenhouse gas which has a high global warming potential into the atmosphere. Early detection of refrigerant leaks could significantly decrease the amount of HCFCs and HFCs in the atmosphere, and reduce global warming and greenhouse gas emissions. Low-refrigerant charge is one of the most common A/C unit service problems, causing numerous insufficient cooling service calls on the first hot day of the year. This surge of service calls on the same day presents a problem to HVAC service contractors because they are not staffed to respond to all the calls in a timely manner.

FIG. 5. Since indoor air temperature is not monitored in this RMS embodiment, a low refrigerant charge alarm will only occur when the compressor discharge refrigerant temperature is at least 25° F. warmer than the baseline polynomial calculates. This will prevent false alarms from occurring due to the 15° F. compressor discharge refrigerant temperature range that could occur under normal operation.

FIG. 6 displays baseline performance, non-critical alarm, and critical alarm curves for a 3-ton split air conditioning system. The equation for the second-order baseline polynomial is:

$$\text{Baseline} = -0.0347 T_{amb}^2 + 6.7064 T_{amb} - 185.05$$

Where $T_{amb}$ is the outdoor ambient air temperature in degrees Fahrenheit.

Using this equation, the OCU-ED can compare any future compressor discharge temperature to the expected value (determined at that particular outdoor ambient air temperature). The non-critical low charge alarm curve and critical low charge alarm curve y-intercepts are 25° F. and 45° F. greater than the baseline y-intercept value, respectively.

Non-Critical Low-Charge Alarm=Baseline+25 or $$\text{Non-Critical Low-Charge Alarm} = -0.0347 T_{amb}^2 + 6.7064 T_{amb} - 160.05$$

Critical Low-Charge Alarm=baseline+45 or $$\text{Critical Low-Charge Alarm} = -0.0347 T_{amb}^2 + 6.7064 T_{amb} - 140.05$$

FIG. 6 displays the compressor discharge refrigerant temperature under several inefficient or failure conditions. The loss of 1, 2, or 3 pounds of refrigerant will increase compressor discharge temperatures by 35° F., 75° F., or 120° F., respectively, and the other system faults of Table 1 are clearly differentiated from the low refrigerant charge data (as will be discussed below).

Since the RMS function is to identify a problem as quickly as possible (while eliminating the possibility of false negatives), the RMS microprocessor need only identify compressor discharge temperatures that are more than 25° F. greater than the baseline curve. A compressor discharge temperature that is more than 25° F. above the baseline indicates that the cooling capacity has decreased by at least 13%, and the coefficient of performance has been reduced by at least 5%. Therefore, it is clear that we can detect very small losses in refrigerant (under one pound loss of charge) as well as the resulting loss of cooling capacity (13%), which would be undetectable by the equipment owner due to higher A/C unit duty cycle. Likewise, an efficiency degradation of 5% might not be detected by equipment owners on their energy bill, but will be detected by the RMS according to the present invention before the problem worsens. These very small reductions in performance can be detected by the RMS while avoiding the potential for false positives. Note that the maximum temperature differential that can exist due to variations in the unknown interior air temperature is only 15° F., and the 25° F. variation above the baseline was selected to be well above the potential 15° F. normal variation due to different possible normal indoor air temperatures.

We have also discovered that if the indoor air temperature is correlated with the compressor discharge refrigerant temperature instead of the outdoor air temperature, then the deviation from the baseline that indicates a low of refrigerant charge could be tightened from 25° F. to 20° F., further improving the sensitivity of the RMS to detect even smaller deviations in performance and even smaller losses of charge. However, our currently preferred embodiment uses only the compressor discharge temperature with the outdoor ambient air temperature since this can detect sufficiently small changes in capacity and refrigerant charge without requiring an additional ED or attempting to measure indoor air temperature with the AP that will be located next to a heat source (computer) which may distort the temperature reading.

Furthermore, if indoor and outdoor air temperatures are used to correlate compressor discharge refrigerant temperature, the offset from baseline can be further reduced for maximum monitoring precision.

Failure Mode 2: Low Starting Torque Caused by Low Run Capacitance

Three methods can be used to determine if the starting torque is diminishing due to a faulty capacitor. In the simplest method, the ratio of the start windings voltage to the run winding voltage (or the inverse) as a function of condensing unit or compressor current draw of the normally operating baseline system can be compared to the measured value of this voltage ratio over time. A decrease of more than 5% in the measured voltage ratio value when compared to the baseline normal predicted value (evaluated at the current draw), indicates a warning that the capacitance of the run capacitor has degraded and the capacitor should be replaced even though the unit remains operational. A decrease of more than 10% in the measured voltage ratio value when compared to the baseline normal predicted value (evaluated at the current draw), indicates a severe problem since the capacitance of the run capacitor has degraded to the point that the system may not start on a hot day and the capacitor should be replaced as soon as possible.

In the currently preferred embodiment, a baseline of the winding voltage ratio (start winding voltage divided by run winding voltage or the inverse) versus the total current is established during the learning period to detect low run capacitance. After a sufficient learning period when a large enough current range has been completed, a best-fit second order polynomial baseline is then calculated. When the winding voltage ratio for a given current is less than 95% of the predicted value, a low priority warning of low capacitance is indicated. When the winding voltage ratio is less than 90% of the predicted value, a high priority warning of low capacitance is indicated.

In addition to our novel approach, two widely accepted methods are available. However these methods would significantly increase cost and complexity. One method involves directly measuring the capacitance. This can be accomplished by measuring the voltage and current of the capacitor and using i=C*dv/dt to calculate the capacitance. This method is not used in the preferred embodiment because of the extra current sensor required. The other method is to measure the phase offset between the run winding voltage and the start winding voltage; however this requires high-speed sampling and therefore dramatically increases processor speed and data storage requirements. This phase offset will decrease as the capacitance decreases.

We have also discovered that the phase offset variation is less sensitive to the capacitance variation than the preferred method.

Example 2: Demonstrating the Capability to Identify Low Run Capacitance

FIG. 9 shows the variation in winding voltage ratio as a function of current at different run capacitances for a condensing unit. The particular condensing unit used in this example specified a 45 uF run capacitor. The normalized winding voltage ratio of a 45 μF capacitor was used as the baseline data. In this example, the equation for the baseline curve was $$\text{Baseline}=-0.0004I^2-0.15I+1.2203$$

where 1 is the current draw of the unit. The current draw used to establish the coefficients of the second order polynomial are determined from initial operating data during the learning process and either the compressor current draw or the current draw of the entire outdoor unit can be utilized as long as the current being measured is consistent. That is the current draw being used to learn must be the same as the current draw used during subsequent monitoring The non-critical and critical alarm curves are at normalized winding values of 95% and 90% of the baseline curve, respectively.

$$\text{Non-Critical Low Run Capacitance}=0.95*\text{Baseline}$$

or $$\text{Non-Critical Low Run Capacitance}=0.95(-0.0004I^2-0.15I+1.2203)$$

$$\text{Critical Low Run Capacitance}=0.90*\text{Baseline}$$

or $$\text{Non-Critical Low Run Capacitance}=0.90(-0.0004I^2-0.15I+1.2203)$$

The data was collected at multiple temperatures for each capacitance to vary current draw. It can be seen that the slope of the winding voltage ratio to current is the same at lower run capacitances and only the y-intercept changes. This observation is used to determine the thresholds which are scaled second order polynomials of the baseline. While a higher order curve fit of the data could of course be used, we have discovered that a simple second order polynomial curve fit is sufficient.

Failure Mode 3: Low Starting Torque Caused by Faulty Potential Relay or Degraded Start Capacitor The same method used in Failure Mode 2 and discussed in Example 2, namely the variation in the winding ratio, is used to identify a low run capacitance. However for Start Capacitor and Potential Relay monitoring, only the transient change in this behavior during the initial start-up of the compressor is used, since the potential relay switches the start capacitor out of the circuit rapidly after start up. Alternatively, we can monitor the time it takes for the start winding to come up to running voltage as a start cap failure indicator. For the potential relay, we can observe the winding voltage ratio after the start winding rises to determine if the relay opened.

Failure Mode 4—Diminished Condenser Airflow

To detect diminished condenser airflow, a baseline curve of condenser outlet refrigerant temperature (measured on the external surface of the condenser outlet piping to reduce cost) verses outdoor ambient temperature is determined in the baseline data collection period. Once this second-order best-fit polynomial has been established mathematically, the OCU-ED calculates the expected value during A/C unit monitoring using the outdoor air temperature. If the measured condenser outlet temperature is more than 6° F. above the predicted value from the baseline curve (represents 37% blockage), diminished condenser airflow will be indicated if the compressor discharge temperature is within the normal range. A condenser coil that is 37% blocked will result in a deviation from the baseline (normal) liquid line temperature curve of 6° F. However, just a deviation from the liquid line temperature baseline curve is not sufficient to identify decreased condenser airflow because a system lacking refrigerant charge can also cause a 5° F. increase in liquid line temperature. Therefore, to identify insufficient condenser airflow, as opposed to some other problem, the liquid line must be at least 6° F. greater than the baseline value and the compressor discharge temperature must be within 15° F. of the baseline (which indicates the A/C unit is sufficiently charged). While these two tests are sufficient to accurately detect reduced condenser airflow, we have also discovered that an additional identifying trait is the increased current draw. Specifically, the current draw can be compared to the baseline performance current curve and the current draw should be at least 0.3 amperes more than the baseline value if the condenser flow is reduced (see Table 2 below). The normal baseline current draw is also evaluated using the measured outdoor air temperature).

It will now be understood by one skilled in the art that a key aspect of this invention is to use the condenser liquid outlet temperature, measured on the external refrigerant piping just downstream of the condenser, as an indicator of system problems related to decreased condenser airflow if a prior problem of low-charge was not indicated. The actual variation to be used to detect a problem is dependent on the level of detection desired by the designer. It should also be noted that the condenser liquid line temperature increases with outdoor air temperature, but indoor air temperature has a negligible effect on the condenser outlet temperature data as can be seen in (FIG. 8). The insensitivity to indoor air temperature is significant since indoor air temperature is not being monitored in order to reduce system monitoring cost complexity. Once again, to reduce the cost of the temperature sensor, this condenser refrigerant outlet temperature is measured on the exterior surface of the tubing downstream of the condenser. Since the baseline behavior is learned after the sensor is installed, the exact location of the temperature sensor downstream of the condenser is not critical, but of course, must be near enough to avoid any temperature effects, such as sunlight, which would not be directly related to the condenser refrigerant exit temperature.

Example 4. Experimental Demonstration of the Faulty Condenser Airflow Detection Method FIG. 8 displays the baseline, non-critical alarm, and critical alarm curves for condenser blockages which were calculated after baseline data collection. The baseline curve equation in this example is Baseline=$0.0369T_{amb}^2 - 5.27T_{amb} + 270.10$ where $T_{amb}$ is the outdoor air temperature.
The non-critical condenser blockage alarm curve and critical condenser blockage alarm curve values are 6° F. and 10° F. greater than the baseline curve y-intercept.

Non-Critical Condenser Air Blockage=Baseline+6 or

Non-Critical Condenser Air Blockage=$0.0369T_{amb}^2 - 5.27T_{amb} + 276.10$

Critical Condenser Air Blockage=Baseline+10 or

Critical Condenser Air Blockage=$0.0369T_{amb}^2 - 5.27T_{amb} + 280.10$

FIG. 8 displays the measured values obtained when operating with each of the failure modes identified in Table 1 and how they compare to the thresholds for non-critical and critical arm notifications. As shown in FIG. 8 a condenser coil that is 37% blocked will result in a deviation from the baseline (normal) liquid line temperature curve of 6° F. However, as stated earlier, a deviation from the liquid line temperature baseline curve is not sufficient to identify low condenser airflow because a system lacking one pound of refrigerant charge will also cause a 6° F. increase in liquid line temperature. Therefore, to identify insufficient condenser airflow, the liquid line must be at least 6° F. greater than the baseline value and the compressor discharge temperature must be within 15° F. of the baseline (which indicates the A/C unit is sufficiently charged). In this case, the 6° F. offset from baseline will allow early detection of a 37% blocked or restricted airflow condition, which translates into a 1% reduction in cooling capacity and a 7% reduction in the system's Coefficient of Performance. The potential variation from the baseline curve, due to not knowing the interior temperature, has been shown to cause less than a 4° F. differential in liquid line temperature due to indoor air temperature variation (see FIG. 8), therefore, indoor air temperature need not be monitored. Of course, if the indoor air temperature is known, the tolerances for predicting a problem can, of course, be improved. A second end device communicating with the existing AP and reporting indoor air temperature among other data could of course be implemented within the scope of the present invention. This IAH-ED could also be used to both monitor and control the indoor air temperature, by activating the control of the system, thereby acting as a thermostat control of the system.

These very small reductions in cooling capacity and performance can be detected while avoiding the potential for false positives. Note that the maximum temperature differential that can exist due to variations in the unknown interior air temperatures is only 2° F. to 4° F. The 6° F. variation above the baseline was selected to be above the maximum potential 4° F. normal variation due to different possible normal interior temperatures. Once again, with the implementation of the indoor air monitoring optional end device, the interior structure temperature will be known and the deviation from the baseline can be tightened from 6° F. to 4° F., further improving the sensitivity of the RMS to detect even smaller reductions in cooling capacity and performance.

A complete condenser airflow failure, such as condenser fan failure, will cause condenser saturation temperature to rise until the compressor's internal cutoff trips due to high electrical current. Our RMS can monitor the number of cycles and cycle duration to identify short cycling. In typical RMS operation, the first five minutes of data are discarded to avoid transient readings. But if an A/C unit short cycles three consecutive times, (determined by looking at current draw), the RMS will observe the last liquid line temperature to determine if the condenser fan has failed. A condenser fan failure will cause condenser liquid line temperatures that are at least 40° F. greater than the baseline condenser liquid line temperature.

Failure Mode 5—Diminished Evaporator Airflow

As stated earlier, slight reductions in evaporator airflow must be ignored since they can be caused by the use of different quality air filters at different times. However, should the evaporator airflow become significantly reduced due to a dirty air filter or reduced blower performance, the RMS will provide an alarm. An 85% blockage of the evaporator airflow rate will result in more than a 0.5 amp decrease in the compressor current (from the baseline performance curve) and a 5° F. decrease in the compressor discharge temperature. These two concurrent symptoms are unique to a severely blocked air filter that requires changing. For example, an 85% reduction in airflow will result in a 25% reduction in cooling capacity and a 17% reduction in COPc.

A total loss of evaporator airflow, caused by a complete blower failure, is indicated by an increase in the compressor discharge temperature of more than 10° F. above the baseline curve and a reduction in the compressor current of more than 1 ampere. These two concurrent symptoms are unique to a blower failure and demonstrate that the A/C unit requires immediate servicing.

Failure Mode 6—Pitted Contactor

Pitted electrical contact surfaces on the contactor make a poor electrical connection, causing excessive electrical resistance and substantial heating of the contact surface, and resulting in further pitting of the contactor. The resistance imposed by the pitted contactor will lower the voltage to the compressor and condenser fan, providing lower starting and operating torque to these electric motors. Since the RMS measures the voltage both upstream and downstream of the contactor, the voltage drop across the contactor caused can be determined. The voltage drop will be divided by the current to determine the contact resistance. An increase in the contactor resistance to more than double the originally measured resistance will be flagged as a low-priority warning. A contactor resistance of 5 times the original resistance will be flagged as an immediate high-priority (imminent failure) service problem.

RMS Logic to Generate the Baseline Performance Data

Since thousands of combinations of different condensing units (rated for different efficiencies, power inputs, and refrigerants), air handlers, expansion devices, air filters, and blower motor speed settings exist, it is unrealistic to assume all systems will operate with the same performance curves. Therefore, the RMS must learn the performance of each individual A/C or heat pump system immediately after RMS installation (and after proper A/C system operation is verified by the HVAC technician). The RMS then uses the learned baseline to compare future performance. Faults and health monitoring can then be identified whenever the measured performance deviates too far from the established baseline data.

In the currently preferred embodiment, the RMS performs the following steps to collect the baseline data (also shown in FIG. 10):

1) A trained HVAC/R technician installs the RMS device, completes the system information questionnaire, and activates the reset switch. This technician or some other employee of the service provider must enter the system information onto the web server.
2) When the unit starts, the RMS does not take temperature or voltage and current readings until the OCU has been operating for a minimum amount of time, to allow the system to reach a stable operating condition for the current outdoor ambient temperature. In the currently preferred embodiment, five minutes of operation has been shown to be sufficient for the sensor readings to achieve reasonably stable, steady state conditions.
3) When the unit is operating within the Temperature Learning Range, the RMS records the data from each sensor at regular intervals. In the currently preferred embodiment, the time interval for temperature readings is 30-seconds and the time intervals for current and voltage sensors are five-seconds. In the current embodiment, data is recorded over a five-minute interval for each data point. When all data storage spaces are filled at the end of the five minute interval, the next data point overwrites the oldest piece of data. Therefore, only the most recent five minutes of data are stored on the OCU-ED. Upon cycle stop or after one hour of continuous A/C operation, these recorded data points (for each sensor) are analyzed for statistical accuracy (to eliminate outliers) and then averaged. Of course, one skilled in the art could use other data sampling methods.
4) To calculate accurate system performance algorithms over the typical range of outdoor air temperature during A/C operation, Baseline Performance Data must be collected over the Temperature Learning Range. These data are referred to as Baseline Performance Data. If the baseline performance data sets are not complete, the OCU-ED will attempt to add the new data point to the Baseline Performance Data set. If the averaged outdoor air temperature of the last data point is at least 1° F. from any existing baseline data point, it is saved as a baseline data point. Once the last data point is saved to the Baseline Performance Data or discarded if the data point for that temperature already exists, the process goes back to Step 2 if more Baseline Performance Data points are needed or proceed to Step 5 if the Baseline Performance Data is complete.
5) Once Baseline Performance Data is collected, the OCU-ED either transmits the Baseline Performance Data to the server (via the AP), and the server then calculates performance algorithms for each individual sensor, or these calculations can be performed locally on the OCU-ED. For the currently preferred embodiment, these algorithms are second-order, best-fit polynomials of the Baseline Performance Data and describe acceptable system performance when the unit is operating correctly. Once Baseline Performance Algorithms are calculated with respect to outdoor air temperature, they can be saved on the server, downloaded for storage on the OCU-ED, or both.

The Learning Process can be completed in as little as one day/night operation of the A/C unit. The system can relearn the A/C unit anytime a service technician believes a major repair or tune-up to the system has occurred and the Relearn Switch has been actuated. This can be accomplished by pressing the momentary reset switch or via a software setting.

After performance data is analyzed and averaged, all data collected in the future is compared to the Baseline Performance Algorithms. This comparison can be performed locally and/or remotely. Faults are identified when the new data fall too far from the expected performance that is calculated using the outdoor air temperature and Baseline Performance Algorithms.

A Currently Preferred Embodiment of the RMS Health Monitoring Logic

Given the disclosure herein, one skilled in the art can now envision other ways to compare the measured data with the baseline performance curves. One currently contemplated and preferred approach is now described (FIG. 11).

Once the RMS has learned a particular system:
1) Using polynomials to curve fit the learned normal behavior, the OCU-ED or the host computer calculates the expected compressor discharge temperature, condenser liquid line outlet temperature, and condensing unit (or compressor) current draw for the particular measured outdoor air temperature. In the currently preferred embodiment, a second order polynomial is used to fit this data. Using a polynomial, the OCU-ED or the host computer calculates the expected start winding to run winding voltage ratio for the particular measured current. In the currently preferred embodiment, a second order polynomial is used to fit this learned normal voltage ratio data.
2) The data collected at the end of every A/C system cycle (the last 5 minutes of operation is captured using the same method used in the learning process) is compared to the Baseline Performance Value (determined at the average outdoor air temperature or current).
3) If the last data point falls too far from the expected baseline data point, the OCU-ED sends a packet of information to the AP to be relayed to the host computer (the server), and the reporting frequency is increased.
4) The server processes the data to ensure they are consistent and repeatable before raising an alarm.

A Currently Preferred Embodiment to Determine Critical or Non-Critical Alarm Status The RMS can identify not only A/C system problems, but also categorize the severity of the problem depending on the potential for an immediate failure. High priority critical alarms have the potential to damage A/C equipment, fail immediately, or cause mold problems since building humidity is not being controlled. These failed systems must be serviced immediately. Lower priority alarms refer to situations causing inefficient operation or decreased cooling capacity, but immediate servicing is not required to prevent equipment damage or eminent failure. These alarm distinctions allow the HVAC technician to prioritize the service calls by servicing critical alarms first and then units with non-critical alarms when they have time.

Contractors and equipment owners do not want an RMS that produces false alarms or fails to identify problems. Therefore, we have developed the following features in the described embodiment to eliminate the possibility of false alarms or unidentified problems:
  Eliminate transient effects—The RMS OCU-ED will discard data collected during the first five minutes of operation and will only analyze data collected during the last five minutes of operation. Experimental data showed that the time-averaged data of the first five minutes of operation did not accurately represent system performance. However, the system performance from five to ten minutes after cycle start was an accurate representation of steady-state performance.
  Collect several data points and obtain average values—The RMS will store the last ten data points for each sensor to allow time-averaging over a five-minute span of operation.
To assure the data recorded represents steady state and not transient data, the data will be obtained after the unit has been operating for a sufficient period of time, typically more than five minutes of operation. One method to do this is to continually record the last five minutes of data, overwriting the same data storage locations. In this way, the last data saved, represents the data that was collected during the last five minutes of operation (just before the A/C is cycled off). For long periods of operation, the last five minutes of every hour of uninterrupted operation can be used. These methods are, generally speaking, well known in the art.
  Eliminate spurious data points—Prior to time-averaging the data points, the RMS will perform simple statistical verification to the data and eliminate any outliers that may skew the averages. If the data scatter is too large, the entire data set will be repeated.
  The baseline data performance curves are only meant to be accurate within the 70° F. to 95° F. outdoor air temperature range. Increasing this temperature range would require unacceptable extrapolation or baseline data collection that could last months. Therefore, data points with outdoor air temperature averages that fall outside of the Temperature Learning Range are discarded. While some data points on cooler or hotter days will be discarded, data will be collected within the Temperature Learning Range during the afternoon, night, and/or morning of those same days so that alarm conditions will still be promptly identified without inaccurate extrapolation.
  One individual alarm reading will not trigger the alarm notification. In the current embodiment, three consecutive alarm readings for the same critical problem are required to trigger a critical alarm, while ten consecutive alarms are required for non-critical alarm notification.

Table 2 briefly summarizes A/C unit conditions that can be identified, the way in which the RMS identifies the condition, the accuracy of the detection, and the system inefficiency when the problem is identified.

TABLE 2

Ability of RMS to detect power consumption increase or cooling capacity degradation

| Condition | Means of Identification | Detection Accuracy |
| --- | --- | --- |
| Low refrigerant charge | Compressor discharge temp > baseline + 25° F. | 1 lb low charge 13% reduced capacity 5% reduced COPc |
| Failed Run Capacitor | Winding Voltage Ratio < 0.95 | 28% reduction in run capacitance |
| Blocked or Restricted Condenser Airflow | Liquid line temp > Baseline + 6° F. AND Current draw > Baseline + A AND Compressor discharge temp < baseline + 15° F. | 37% condenser blockage 1% reduced capacity 7% reduced COPc |
| Blocked or Restricted Evaporator Airflow | Current draw < Baseline − 0.5 A AND Compressor discharge temp < baseline − 5° F. | 80% blockage 12% reduced capacity 9% reduced COPc |
| Pitted Contactor | Voltage Drop Across the Contactor and current flow | Any significant increase in contactor resistance (>5%) |

While we have shown and described a currently preferred embodiment of our invention, it should be understood that the same is susceptible to changes and modifications without departing from the scope of our invention. For example, one skilled in the art will readily appreciate that this invention will work for any vapor compression thermal control system including but not limited to refrigerators, freezers, cryocoolers, air conditioners, dehumidifiers, heat pumps, water coolers, and the like. Therefore, we do not intend to be limited to the details shown and described but intend to cover all such changes and modifications as are encompassed by the scope of the appended claims.

We claim:

1. An end device useable in a monitoring system for at least one vapor compression system having outdoor components that include an outdoor compressor and an outdoor condenser, the end device having an outside air temperature sensor, a temperature sensor operatively arranged at one of the inlet side and the discharge side of the outdoor compressor and means for comparing data of the temperature sensors with data that has been previously obtained during normal operation of the at least one vapor compression system, wherein the end device is configured to determine solely on the basis of the compared data that the at least one vapor compression system is or is not subsequently in normal operation.

2. The end device of claim 1, wherein the comparing means is configured to wirelessly transmit the compared data to a receiving device.

3. The end device of claim 1, wherein the compared data includes information concerning an occurrence of periods when the at least one vapor compression system is operating at an abnormal state and is wirelessly transmitted to at least one of the system's custodian and a repair service provider.

4. A method of monitoring performance of at least one vapor compression system, consisting of measuring values of only outdoor air temperature, compressor discharge line temperature, outlet line temperature, current draw, and ratio of start-winding voltage to run-winding voltage, and comparing the measured values with values of the outdoor air temperature, compressor discharge line temperature, condenser outlet line temperature, current draw, and ratio of start-winding voltage to run-winding voltage that have been previously obtained during proper system operation.

5. The method of claim 4, wherein the comparing step is performed at comparable outdoor air temperature values obtained during normal operation.

6. A method of monitoring performance of at least one vapor compression or heat pump system, consisting of measuring outdoor air temperature and temperature at one of an inlet side and a discharge side of a compressor of each of the at least one system, and comparing values of the measured outdoor and compressor temperatures with one of measured and predicted values that have been previously obtained during proper system operation at the same outdoor ambient temperature for determining that the at least one system is or is not subsequently operating properly.

7. The method of claim 6, wherein results of the compared values are wirelessly transmitted to at least one of a custodian and a repair service provider for the at least one system.

8. A method of monitoring performance of an evaporator of a vapor compression system, consisting of measuring outdoor ambient temperature and temperature at one of a discharge side and an inlet side of a compressor of the system, and comparing values of the measured temperatures with measured or predicted values previously obtained during proper system operation at the same outdoor ambient temperature.

9. The method of claim 8, wherein results of the compared values are wirelessly transmitted to at least one of a custodian and a repair service provider for the system.

* * * * *